US008062877B2

(12) United States Patent
Xiao et al.

(10) Patent No.: US 8,062,877 B2
(45) Date of Patent: Nov. 22, 2011

(54) PECTATE LYASES WITH INCREASED THERMOSTABILITY AND/OR ENZYMATIC ACTIVITY

(75) Inventors: Zhizhuang Xiao, Toronto (CA); Hélène Bergeron, St.-Mathieu-du-Parc (CA); Stephan Grosse, Longueuil (CA); Peter C. K. Lau, Kirkland (CA)

(73) Assignee: National Research Council of Canada, Ohawa (CA)

( * ) Notice: Subject to any disclaimer, the term of this patent is extended or adjusted under 35 U.S.C. 154(b) by 134 days.

(21) Appl. No.: 12/451,346

(22) PCT Filed: May 5, 2008

(86) PCT No.: PCT/CA2008/000867

§ 371 (c)(1), (2), (4) Date: Nov. 9, 2009

(87) PCT Pub. No.: WO2008/138109

PCT Pub. Date: Nov. 20, 2008

(65) Prior Publication Data

US 2010/0285569 A1 Nov. 11, 2010

Related U.S. Application Data

(60) Provisional application No. 60/924,386, filed on May 11, 2007.

(51) Int. Cl.

| | |
|---|---|
| *C12N 9/00* | (2006.01) |
| *C12N 9/88* | (2006.01) |
| *C12N 1/20* | (2006.01) |
| *C12N 15/00* | (2006.01) |
| *C07H 21/04* | (2006.01) |

(52) U.S. Cl. ..................... 435/232; 435/183; 435/252.3; 435/320.1; 536/23.2

(58) Field of Classification Search ........................ None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Hans Koenig

(57) ABSTRACT

Using site-directed mutagenesis to mutate the *Xanthomonas campestris* pectate lyase gene, variants of *Xanthomonas campestris* pectate lyase with improved thermostability and/or enzymatic activity have been expressed in *Escherichia coli*, and then isolated and purified. The mutant *Xanthomonas campestris* pectate lyases are more effective than the wild-type enzyme, also expressed in *E. coli*, in removing pectic compounds from natural hemp fiber.

14 Claims, 5 Drawing Sheets

```
NP_638163    ------------------GPVGYGAATTGGGNKVPVNVATFEAMQSAIDSYSGS------ 59
CAD56882     ASALNSGKVNPLADFSLKGFAALNGGTTGGEGGQTVTVTTGDQLIAALKNKNAN------ 54
BAB40336     ------KELGHEVLKPYDGWAAYGEGTTGGAMASPQNVFVVTNRTELIQALGGNNHTNQY 54
AAD35518     -----ASLNDKPVGFASVPTADLPEGTVGGLGGEIVFVRTAEELEKYTTAEGKY------ 49
                                 .    .*.**       * .           .

NP_638163    --GGLVLNYTGKFDFGTIKDVCAQ------------------------------------ 81
CAD56882     --TPLKIYVNGTITTS-------------------------------------------- 68
BAB40336     NSVPKIIYVKGTIDLNVDDNNQPVGPDFYKDPHFDFEAYLREYDPATWGKKEVEGPLEEA 114
AAD35518     -----VIVVDGTIVFE-------------------------------------------- 60
                   :   *.:

NP_638163    ----WKLPAKTVQIKNKSDVTIKG--ANGSAANFGIRVVGNAHNVIIQNMTIGLLQGGE- 134
CAD56882     -----NTSASKIDVKDVSNVSIVGSGTKGELKGIGIKIWR-ANNIIIRNLKIHEVASG-- 120
BAB40336     RVRSQKKQKDRIMVYVGSNTSIIGVGKDAKIKGGGFLIKN-VDNVIIRNIEFEAPLDYFP 173
AAD35518     ---------PKREIKVLSDKTIVG-INDAKIVGGGLVIKD-AQNVIIRNIHFEGFYMEDD 109
                          :   *: :* *   ...  . *: :   ..*:**:*: :

NP_638163    --------------DADSISLEGNSSGEPSKIWVDHNTVFA------SLTKCSGAGDASF 174
CAD56882     --------------DKDAIGIEGPSK----NIWVDHNELYH------SLN----VDKDYY 152
BAB40336     EWDPTDGTLGEWNSEYDSISIEGSSH-----IWIDHNTFTDGDHPDRSLGTYFGRPFQQH 228
AAD35518     PRGK--------KYDFDYINVENSHH-----IWIDHCTFVN-----------------GN 139
                           : * *.:*.        **:**  .

NP_638163    DGGIDMKKGVHHVTVSYNYVYNYQKVALNGYSDSDTKNS---AARTTYHHNRFENVESRV 231
CAD56882     DGLFDVKRDAEYITFSWNYVHDGWKSMLMGSSDSDNYN-----RTITFHHNWFENLNSRV 207
BAB40336     DGALDIKNSSDFITISYNVFTNHDKVTLIGASDSRMADSG--HLRVTLHHNYYKNVTQRL 286
AAD35518     DGAVDIKKYSNYITVSWCKFVDHDKVSLVGSSDKEDPEQAGQAYKVTYHHNYFKNCIQRM 199
             ** .*:*.  ..:*.*:  . :  *  * * **.   :        * *** ::*  .*:

NP_638163    PLQRRGLSHIYNNYFNNVTTSGIN----------VRMGGIAKIESNYFEN---------- 271
CAD56882     PSFRFGEGHIYNNYFNKIIDSGIN----------SRMGARIRIENNLFEN---------- 247
BAB40336     PRVRFGQVHIYNNYYEFSNLADYD----------FQYAWGVGVFSQIYAQNNYFSFDWDI 336
AAD35518     PRIRFGMAHVFNNFYSMGLRTGVSGNVFPIYGVASAMGAKVHVEGNYFMGYGAVMAEAG- 258
             *  * *  *::**::.    :. .             .    : .: :

NP_638163    IKNPVTSRDSSEIGYWDLINNYVGSGITWGTPDGSKPYANATNWISTKVFPESLGYIYTV 331
CAD56882     AKDPIVSWYSSSPGYWHVSNNKFVN------SRGSMPTTSTTTYNPP--------YSYSL 293
BAB40336     DPSLIIKVWSKNEESMYETGTIVDLPNGRRYIDLVASYNESNTLQLKKEVTWKPMFYHVI 396
AAD35518     IAFLPTRIMGPVEGYLTLGEGDAKNEFYYCKEPEVRPVEEGKPALDPRE-----YYDYTL 313
                      .                          .  . .             : : :

NP_638163    TPAAQVKAKVIATAGAGKNLAE------ 353
CAD56882     DNVDNVKSIVKQNAGVGKINP------- 314
BAB40336     HPTPSVPALVKAKAGAGNLH-------- 416
AAD35518     DPVQDVPKIVVDGAGAGKLVFEELNTAQ 341
               . .*   *   **.*:

NP_638163  = SEQ ID NO: 1
CAD56882   = SEQ ID NO: 24
BAB40336   = SEQ ID NO: 25
AAD35518   = SEQ ID NO: 26
```

FIG. 1

SEQ ID NO: 1 – parent *Xc*PL

MTSKTLQGALALALSACAAGAIAGPVGYGAATTGGGNKVPVNVATFEAMQSAIDSYSGSGGLVLNYTGKFDF
GTIKDVCAQWKLPAKTVQIKNKSDVTIKGANGSAANFGIRVVGNAHNVIIQNMTIGLLQGGEDADSISLEGN
SSGEPSKIWVDHNTVFASLTKCSGAGDASFDGGIDMKKGVHHVTVSYNYVYNYQKVALNGYSDSDTKNSAAR
TTYHHNRFENVESRVPLQRRGLSHIYNNYFNNVTTSGINVRMGGIAKIESNYFENIKNPVTSRDSSEIGYWD
LINNYVGSGITWGTPDGSKPYANATNWISTKVFPESLGYIYTVTPAAQVKAKVIATAGAGKNLAE

SEQ ID NO: 3 - Mutant A31G

MTSKTLQGALALALSACAAGAIAGPVGYGAGTTGGGNKVPVNVATFEAMQSAIDSYSGSGGLVLNYTGKFDF
GTIKDVCAQWKLPAKTVQIKNKSDVTIKGANGSAANFGIRVVGNAHNVIIQNMTIGLLQGGEDADSISLEGN
SSGEPSKIWVDHNTVFASLTKCSGAGDASFDGGIDMKKGVHHVTVSYNYVYNYQKVALNGYSDSDTKNSAAR
TTYHHNRFENVESRVPLQRRGLSHIYNNYFNNVTTSGINVRMGGIAKIESNYFENIKNPVTSRDSSEIGYWD
LINNYVGSGITWGTPDGSKPYANATNWISTKVFPESLGYIYTVTPAAQVKAKVIATAGAGKNLAE

SEQ ID NO: 4 - Mutant R236F

MTSKTLQGALALALSACAAGAIAGPVGYGAATTGGGNKVPVNVATFEAMQSAIDSYSGSGGLVLNYTGKFDF
GTIKDVCAQWKLPAKTVQIKNKSDVTIKGANGSAANFGIRVVGNAHNVIIQNMTIGLLQGGEDADSISLEGN
SSGEPSKIWVDHNTVFASLTKCSGAGDASFDGGIDMKKGVHHVTVSYNYVYNYQKVALNGYSDSDTKNSAAR
TTYHHNRFENVESRVPLQRFGLSHIYNNYFNNVTTSGINVRMGGIAKIESNYFENIKNPVTSRDSSEIGYWD
LINNYVGSGITWGTPDGSKPYANATNWISTKVFPESLGYIYTVTPAAQVKAKVIATAGAGKNLAE

SEQ ID NO: 5 - Mutant A31G/R236F

MTSKTLQGALALALSACAAGAIAGPVGYGAGTTGGGNKVPVNVATFEAMQSAIDSYSGSGGLVLNYTGKFDF
GTIKDVCAQWKLPAKTVQIKNKSDVTIKGANGSAANFGIRVVGNAHNVIIQNMTIGLLQGGEDADSISLEGN
SSGEPSKIWVDHNTVFASLTKCSGAGDASFDGGIDMKKGVHHVTVSYNYVYNYQKVALNGYSDSDTKNSAAR
TTYHHNRFENVESRVPLQRFGLSHIYNNYFNNVTTSGINVRMGGIAKIESNYFENIKNPVTSRDSSEIGYWD
LINNYVGSGITWGTPDGSKPYANATNWISTKVFPESLGYIYTVTPAAQVKAKVIATAGAGKNLAE

FIG. 2

SEQUENCE LISTING

```
<160> NUMBER OF SEQ ID NOS: 26

<210> SEQ ID NO 1
<211> LENGTH: 353
<212> TYPE: PRT
<213> ORGANISM: Xanthomonas campestris

<400> SEQUENCE: 1

Met Thr Ser Lys Thr Leu Gln Gly Ala Leu Ala Leu Ala Leu Ser Ala
1               5                   10                  15

Cys Ala Ala Gly Ala Ile Ala Gly Pro Val Gly Tyr Gly Ala Ala Thr
            20                  25                  30

Thr Gly Gly Gly Asn Lys Val Pro Val Asn Val Ala Thr Phe Glu Ala
        35                  40                  45

Met Gln Ser Ala Ile Asp Ser Tyr Ser Gly Ser Gly Gly Leu Val Leu
    50                  55                  60

Asn Tyr Thr Gly Lys Phe Asp Phe Gly Thr Ile Lys Asp Val Cys Ala
65                  70                  75                  80

Gln Trp Lys Leu Pro Ala Lys Thr Val Gln Ile Lys Asn Lys Ser Asp
                85                  90                  95
```

```
Val Thr Ile Lys Gly Ala Asn Gly Ser Ala Ala Asn Phe Gly Ile Arg
            100                 105                 110

Val Val Gly Asn Ala His Asn Val Ile Ile Gln Asn Met Thr Ile Gly
        115                 120                 125

Leu Leu Gln Gly Gly Glu Asp Ala Asp Ser Ile Ser Leu Glu Gly Asn
    130                 135                 140

Ser Ser Gly Glu Pro Ser Lys Ile Trp Val Asp His Asn Thr Val Phe
145                 150                 155                 160

Ala Ser Leu Thr Lys Cys Ser Gly Ala Gly Asp Ala Ser Phe Asp Gly
                165                 170                 175

Gly Ile Asp Met Lys Lys Gly Val His His Val Thr Val Ser Tyr Asn
            180                 185                 190

Tyr Val Tyr Asn Tyr Gln Lys Val Ala Leu Asn Gly Tyr Ser Asp Ser
        195                 200                 205

Asp Thr Lys Asn Ser Ala Ala Arg Thr Thr Tyr His His Asn Arg Phe
    210                 215                 220

Glu Asn Val Glu Ser Arg Val Pro Leu Gln Arg Arg Gly Leu Ser His
225                 230                 235                 240

Ile Tyr Asn Asn Tyr Phe Asn Asn Val Thr Thr Ser Gly Ile Asn Val
                245                 250                 255

Arg Met Gly Gly Ile Ala Lys Ile Glu Ser Asn Tyr Phe Glu Asn Ile
            260                 265                 270

Lys Asn Pro Val Thr Ser Arg Asp Ser Ser Glu Ile Gly Tyr Trp Asp
        275                 280                 285

Leu Ile Asn Asn Tyr Val Gly Ser Gly Ile Thr Trp Gly Thr Pro Asp
    290                 295                 300

Gly Ser Lys Pro Tyr Ala Asn Ala Thr Asn Trp Ile Ser Thr Lys Val
305                 310                 315                 320

Phe Pro Glu Ser Leu Gly Tyr Ile Tyr Thr Val Thr Pro Ala Ala Gln
                325                 330                 335

Val Lys Ala Lys Val Ile Ala Thr Ala Gly Ala Gly Lys Asn Leu Ala
            340                 345                 350

Glu


<210> SEQ ID NO 2
<211> LENGTH: 353
<212> TYPE: PRT
<213> ORGANISM: Xanthomonas campestris
<220> FEATURE:
<221> NAME/KEY: MISC_FEATURE
<222> LOCATION: (31)..(31)
<223> OTHER INFORMATION: Xaa is alanine or glycine
<220> FEATURE:
<221> NAME/KEY: MISC_FEATURE
<222> LOCATION: (236)..(236)
<223> OTHER INFORMATION: Xaa is arginine or phenylalanine with the
      proviso that it is not arginine when Xaa at position 31 is alanine

<400> SEQUENCE: 2

Met Thr Ser Lys Thr Leu Gln Gly Ala Leu Ala Leu Ala Leu Ser Ala
1               5                   10                  15

Cys Ala Ala Gly Ala Ile Ala Gly Pro Val Gly Tyr Gly Ala Xaa Thr
            20                  25                  30

Thr Gly Gly Gly Asn Lys Val Pro Val Asn Val Ala Thr Phe Glu Ala
        35                  40                  45

Met Gln Ser Ala Ile Asp Ser Tyr Ser Gly Ser Gly Gly Leu Val Leu
    50                  55                  60
```

-continued

```
Asn Tyr Thr Gly Lys Phe Asp Phe Gly Thr Ile Lys Asp Val Cys Ala
65                  70                  75                  80

Gln Trp Lys Leu Pro Ala Lys Thr Val Gln Ile Lys Asn Lys Ser Asp
                85                  90                  95

Val Thr Ile Lys Gly Ala Asn Gly Ser Ala Ala Asn Phe Gly Ile Arg
            100                 105                 110

Val Val Gly Asn Ala His Asn Val Ile Ile Gln Asn Met Thr Ile Gly
        115                 120                 125

Leu Leu Gln Gly Gly Glu Asp Ala Asp Ser Ile Ser Leu Glu Gly Asn
    130                 135                 140

Ser Ser Gly Glu Pro Ser Lys Ile Trp Val Asp His Asn Thr Val Phe
145                 150                 155                 160

Ala Ser Leu Thr Lys Cys Ser Gly Ala Gly Asp Ala Ser Phe Asp Gly
                165                 170                 175

Gly Ile Asp Met Lys Lys Gly Val His His Val Thr Val Ser Tyr Asn
            180                 185                 190

Tyr Val Tyr Asn Tyr Gln Lys Val Ala Leu Asn Gly Tyr Ser Asp Ser
        195                 200                 205

Asp Thr Lys Asn Ser Ala Ala Arg Thr Thr Tyr His His Asn Arg Phe
    210                 215                 220

Glu Asn Val Glu Ser Arg Val Pro Leu Gln Arg Xaa Gly Leu Ser His
225                 230                 235                 240

Ile Tyr Asn Asn Tyr Phe Asn Asn Val Thr Thr Ser Gly Ile Asn Val
                245                 250                 255

Arg Met Gly Gly Ile Ala Lys Ile Glu Ser Asn Tyr Phe Glu Asn Ile
            260                 265                 270

Lys Asn Pro Val Thr Ser Arg Asp Ser Ser Glu Ile Gly Tyr Trp Asp
        275                 280                 285

Leu Ile Asn Asn Tyr Val Gly Ser Gly Ile Thr Trp Gly Thr Pro Asp
    290                 295                 300

Gly Ser Lys Pro Tyr Ala Asn Ala Thr Asn Trp Ile Ser Thr Lys Val
305                 310                 315                 320

Phe Pro Glu Ser Leu Gly Tyr Ile Tyr Thr Val Thr Pro Ala Ala Gln
                325                 330                 335

Val Lys Ala Lys Val Ile Ala Thr Ala Gly Ala Gly Lys Asn Leu Ala
            340                 345                 350

Glu
```

<210> SEQ ID NO 3
<211> LENGTH: 353
<212> TYPE: PRT
<213> ORGANISM: Xanthomonas campestris

<400> SEQUENCE: 3

```
Met Thr Ser Lys Thr Leu Gln Gly Ala Leu Ala Leu Ala Leu Ser Ala
1               5                   10                  15

Cys Ala Ala Gly Ala Ile Ala Gly Pro Val Gly Tyr Gly Ala Gly Thr
            20                  25                  30

Thr Gly Gly Gly Asn Lys Val Pro Val Asn Val Ala Thr Phe Glu Ala
        35                  40                  45

Met Gln Ser Ala Ile Asp Ser Tyr Ser Gly Ser Gly Gly Leu Val Leu
    50                  55                  60

Asn Tyr Thr Gly Lys Phe Asp Phe Gly Thr Ile Lys Asp Val Cys Ala
65                  70                  75                  80

Gln Trp Lys Leu Pro Ala Lys Thr Val Gln Ile Lys Asn Lys Ser Asp
```

-continued

```
                85                  90                  95

Val Thr Ile Lys Gly Ala Asn Gly Ser Ala Ala Asn Phe Gly Ile Arg
            100                 105                 110

Val Val Gly Asn Ala His Asn Val Ile Ile Gln Asn Met Thr Ile Gly
        115                 120                 125

Leu Leu Gln Gly Gly Glu Asp Ala Asp Ser Ile Ser Leu Glu Gly Asn
    130                 135                 140

Ser Ser Gly Glu Pro Ser Lys Ile Trp Val Asp His Asn Thr Val Phe
145                 150                 155                 160

Ala Ser Leu Thr Lys Cys Ser Gly Ala Gly Asp Ala Ser Phe Asp Gly
                165                 170                 175

Gly Ile Asp Met Lys Lys Gly Val His His Val Thr Val Ser Tyr Asn
            180                 185                 190

Tyr Val Tyr Asn Tyr Gln Lys Val Ala Leu Asn Gly Tyr Ser Asp Ser
        195                 200                 205

Asp Thr Lys Asn Ser Ala Ala Arg Thr Thr Tyr His His Asn Arg Phe
    210                 215                 220

Glu Asn Val Glu Ser Arg Val Pro Leu Gln Arg Arg Gly Leu Ser His
225                 230                 235                 240

Ile Tyr Asn Asn Tyr Phe Asn Asn Val Thr Thr Ser Gly Ile Asn Val
                245                 250                 255

Arg Met Gly Gly Ile Ala Lys Ile Glu Ser Asn Tyr Phe Glu Asn Ile
            260                 265                 270

Lys Asn Pro Val Thr Ser Arg Asp Ser Ser Glu Ile Gly Tyr Trp Asp
        275                 280                 285

Leu Ile Asn Asn Tyr Val Gly Ser Gly Ile Thr Trp Gly Thr Pro Asp
    290                 295                 300

Gly Ser Lys Pro Tyr Ala Asn Ala Thr Asn Trp Ile Ser Thr Lys Val
305                 310                 315                 320

Phe Pro Glu Ser Leu Gly Tyr Ile Tyr Thr Val Thr Pro Ala Ala Gln
                325                 330                 335

Val Lys Ala Lys Val Ile Ala Thr Ala Gly Ala Gly Lys Asn Leu Ala
            340                 345                 350

Glu
```

<210> SEQ ID NO 4
<211> LENGTH: 353
<212> TYPE: PRT
<213> ORGANISM: Xanthomonas campestris

<400> SEQUENCE: 4

```
Met Thr Ser Lys Thr Leu Gln Gly Ala Leu Ala Leu Ala Leu Ser Ala
1               5                   10                  15

Cys Ala Ala Gly Ala Ile Ala Gly Pro Val Gly Tyr Gly Ala Ala Thr
            20                  25                  30

Thr Gly Gly Gly Asn Lys Val Pro Val Asn Val Ala Thr Phe Glu Ala
        35                  40                  45

Met Gln Ser Ala Ile Asp Ser Tyr Ser Gly Ser Gly Gly Leu Val Leu
    50                  55                  60

Asn Tyr Thr Gly Lys Phe Asp Phe Gly Thr Ile Lys Asp Val Cys Ala
65                  70                  75                  80

Gln Trp Lys Leu Pro Ala Lys Thr Val Gln Ile Lys Asn Lys Ser Asp
                85                  90                  95

Val Thr Ile Lys Gly Ala Asn Gly Ser Ala Ala Asn Phe Gly Ile Arg
            100                 105                 110
```

```
Val Val Gly Asn Ala His Asn Val Ile Ile Gln Asn Met Thr Ile Gly
        115                 120                 125

Leu Leu Gln Gly Gly Glu Asp Ala Asp Ser Ile Ser Leu Glu Gly Asn
    130                 135                 140

Ser Ser Gly Glu Pro Ser Lys Ile Trp Val Asp His Asn Thr Val Phe
145                 150                 155                 160

Ala Ser Leu Thr Lys Cys Ser Gly Ala Gly Asp Ala Ser Phe Asp Gly
                165                 170                 175

Gly Ile Asp Met Lys Lys Gly Val His His Val Thr Val Ser Tyr Asn
            180                 185                 190

Tyr Val Tyr Asn Tyr Gln Lys Val Ala Leu Asn Gly Tyr Ser Asp Ser
        195                 200                 205

Asp Thr Lys Asn Ser Ala Ala Arg Thr Thr Tyr His His Asn Arg Phe
    210                 215                 220

Glu Asn Val Glu Ser Arg Val Pro Leu Gln Arg Phe Gly Leu Ser His
225                 230                 235                 240

Ile Tyr Asn Asn Tyr Phe Asn Asn Val Thr Thr Ser Gly Ile Asn Val
                245                 250                 255

Arg Met Gly Gly Ile Ala Lys Ile Glu Ser Asn Tyr Phe Glu Asn Ile
            260                 265                 270

Lys Asn Pro Val Thr Ser Arg Asp Ser Ser Glu Ile Gly Tyr Trp Asp
        275                 280                 285

Leu Ile Asn Asn Tyr Val Gly Ser Gly Ile Thr Trp Gly Thr Pro Asp
    290                 295                 300

Gly Ser Lys Pro Tyr Ala Asn Ala Thr Asn Trp Ile Ser Thr Lys Val
305                 310                 315                 320

Phe Pro Glu Ser Leu Gly Tyr Ile Tyr Thr Val Thr Pro Ala Ala Gln
                325                 330                 335

Val Lys Ala Lys Val Ile Ala Thr Ala Gly Ala Gly Lys Asn Leu Ala
            340                 345                 350

Glu


<210> SEQ ID NO 5
<211> LENGTH: 353
<212> TYPE: PRT
<213> ORGANISM: Xanthomonas campestris

<400> SEQUENCE: 5

Met Thr Ser Lys Thr Leu Gln Gly Ala Leu Ala Leu Ala Leu Ser Ala
1               5                   10                  15

Cys Ala Ala Gly Ala Ile Ala Gly Pro Val Gly Tyr Gly Ala Gly Thr
            20                  25                  30

Thr Gly Gly Gly Asn Lys Val Pro Val Asn Val Ala Thr Phe Glu Ala
        35                  40                  45

Met Gln Ser Ala Ile Asp Ser Tyr Ser Gly Ser Gly Gly Leu Val Leu
    50                  55                  60

Asn Tyr Thr Gly Lys Phe Asp Phe Gly Thr Ile Lys Asp Val Cys Ala
65                  70                  75                  80

Gln Trp Lys Leu Pro Ala Lys Thr Val Gln Ile Lys Asn Lys Ser Asp
                85                  90                  95

Val Thr Ile Lys Gly Ala Asn Gly Ser Ala Ala Asn Phe Gly Ile Arg
            100                 105                 110

Val Val Gly Asn Ala His Asn Val Ile Ile Gln Asn Met Thr Ile Gly
        115                 120                 125
```

-continued

```
Leu Leu Gln Gly Gly Glu Asp Ala Asp Ser Ile Ser Leu Glu Gly Asn
    130                 135                 140

Ser Ser Gly Glu Pro Ser Lys Ile Trp Val Asp His Asn Thr Val Phe
145                 150                 155                 160

Ala Ser Leu Thr Lys Cys Ser Gly Ala Gly Asp Ala Ser Phe Asp Gly
                165                 170                 175

Gly Ile Asp Met Lys Lys Gly Val His His Val Thr Val Ser Tyr Asn
            180                 185                 190

Tyr Val Tyr Asn Tyr Gln Lys Val Ala Leu Asn Gly Tyr Ser Asp Ser
        195                 200                 205

Asp Thr Lys Asn Ser Ala Ala Arg Thr Thr Tyr His His Asn Arg Phe
    210                 215                 220

Glu Asn Val Glu Ser Arg Val Pro Leu Gln Arg Phe Gly Leu Ser His
225                 230                 235                 240

Ile Tyr Asn Asn Tyr Phe Asn Asn Val Thr Thr Ser Gly Ile Asn Val
                245                 250                 255

Arg Met Gly Gly Ile Ala Lys Ile Glu Ser Asn Tyr Phe Glu Asn Ile
            260                 265                 270

Lys Asn Pro Val Thr Ser Arg Asp Ser Ser Glu Ile Gly Tyr Trp Asp
        275                 280                 285

Leu Ile Asn Asn Tyr Val Gly Ser Gly Ile Thr Trp Gly Thr Pro Asp
    290                 295                 300

Gly Ser Lys Pro Tyr Ala Asn Ala Thr Asn Trp Ile Ser Thr Lys Val
305                 310                 315                 320

Phe Pro Glu Ser Leu Gly Tyr Ile Tyr Thr Val Thr Pro Ala Ala Gln
                325                 330                 335

Val Lys Ala Lys Val Ile Ala Thr Ala Gly Ala Gly Lys Asn Leu Ala
            340                 345                 350

Glu


<210> SEQ ID NO 6
<211> LENGTH: 26
<212> TYPE: DNA
<213> ORGANISM: Artificial
<220> FEATURE:
<223> OTHER INFORMATION: Primer

<400> SEQUENCE: 6

gatcgcaggt ccggccggct acggtg                                          26


<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7

caccgtagcc ggccggacct gcgatc                                          26


<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8

gctacggtgc cggcaccacc ggcg                                            24
```

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
cgccggtggt gccggcaccg tagc 24

<210> SEQ ID NO 10
<211> LENGTH: 31
<212> TYPE: DNA
<213> ORGANISM: Artificial
<220> FEATURE:
<223> OTHER INFORMATION: Primer

<400> SEQUENCE: 10
cggcggcctg gtgatcaact acaccggcaa g 31

<210> SEQ ID NO 11
<211> LENGTH: 31
<212> TYPE: DNA
<213> ORGANISM: Artificial
<220> FEATURE:
<223> OTHER INFORMATION: Primer

<400> SEQUENCE: 11
cttgccggtg tagttgatca ccaggccgcc g 31

<210> SEQ ID NO 12
<211> LENGTH: 35
<212> TYPE: DNA
<213> ORGANISM: Artificial
<220> FEATURE:
<223> OTHER INFORMATION: Primer

<400> SEQUENCE: 12
gcctggtgct gaacgtcacc ggcaagttcg acttc 35

<210> SEQ ID NO 13
<211> LENGTH: 35
<212> TYPE: DNA
<213> ORGANISM: Artificial
<220> FEATURE:
<223> OTHER INFORMATION: Primer

<400> SEQUENCE: 13
gaagtcgaac ttgccggtga cgttcagcac caggc 35

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
ctgaactaca ccggcacgtt cgacttcggc 30

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
gccgaagtcg aacgtgccgg tgtagttcag 30

<210> SEQ ID NO 16
<211> LENGTH: 31
<212> TYPE: DNA
<213> ORGANISM: Artificial
<220> FEATURE:
<223> OTHER INFORMATION: Primer

<400> SEQUENCE: 16
gaactacacc ggcaagatcg acttcggcac c 31

<210> SEQ ID NO 17
<211> LENGTH: 31
<212> TYPE: DNA
<213> ORGANISM: Artificial
<220> FEATURE:
<223> OTHER INFORMATION: Primer

<400> SEQUENCE: 17
ggtgccgaag tcgatcttgc cggtgtagtt c 31

<210> SEQ ID NO 18
<211> LENGTH: 33
<212> TYPE: DNA
<213> ORGANISM: Artificial
<220> FEATURE:
<223> OTHER INFORMATION: Primer

<400> SEQUENCE: 18
gcacaacgtg atcatccgga acatgaccat cgg 33

<210> SEQ ID NO 19
<211> LENGTH: 33
<212> TYPE: DNA
<213> ORGANISM: Artificial
<220> FEATURE:
<223> OTHER INFORMATION: Primer

<400> SEQUENCE: 19
ccgatggtca tgttccggat gatcacgttg tgc 33

<210> SEQ ID NO 20
<211> LENGTH: 30
<212> TYPE: DNA
<213> ORGANISM: Artificial
<220> FEATURE:
<223> OTHER INFORMATION: Primer

<400> SEQUENCE: 20
ggcgtgcatc acatcaccgt gtcctacaac 30

<210> SEQ ID NO 21
<211> LENGTH: 30
<212> TYPE: DNA
<213> ORGANISM: Artificial
<220> FEATURE:
<223> OTHER INFORMATION: Primer

<400> SEQUENCE: 21
gttgtaggac acggtgatgt gatgcacgcc 30

<210> SEQ ID NO 22
<211> LENGTH: 30
<212> TYPE: DNA

<213> ORGANISM: Artificial
<220> FEATURE:
<223> OTHER INFORMATION: Primer

<400> SEQUENCE: 22
ccgctgcagc gctttggctt gagccacatc 30

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23
gatgtggctc aagccaaagc gctgcagcgg 30

<210> SEQ ID NO 24
<211> LENGTH: 314
<212> TYPE: PRT
<213> ORGANISM: Bacillus licheniformis

<400> SEQUENCE: 24

```
Ala Ser Ala Leu Asn Ser Gly Lys Val Asn Pro Leu Ala Asp Phe Ser
1               5                   10                  15

Leu Lys Gly Phe Ala Ala Leu Asn Gly Gly Thr Thr Gly Gly Glu Gly
            20                  25                  30

Gly Gln Thr Val Thr Val Thr Thr Gly Asp Gln Leu Ile Ala Ala Leu
        35                  40                  45

Lys Asn Lys Asn Ala Asn Thr Pro Leu Lys Ile Tyr Val Asn Gly Thr
    50                  55                  60

Ile Thr Thr Ser Asn Thr Ser Ala Ser Lys Ile Asp Val Lys Asp Val
65                  70                  75                  80

Ser Asn Val Ser Ile Val Gly Ser Gly Thr Lys Gly Glu Leu Lys Gly
                85                  90                  95

Ile Gly Ile Lys Ile Trp Arg Ala Asn Asn Ile Ile Ile Arg Asn Leu
            100                 105                 110

Lys Ile His Glu Val Ala Ser Gly Asp Lys Asp Ala Ile Gly Ile Glu
        115                 120                 125

Gly Pro Ser Lys Asn Ile Trp Val Asp His Asn Glu Leu Tyr His Ser
    130                 135                 140

Leu Asn Val Asp Lys Asp Tyr Tyr Asp Gly Leu Phe Asp Val Lys Arg
145                 150                 155                 160

Asp Ala Glu Tyr Ile Thr Phe Ser Trp Asn Tyr Val His Asp Gly Trp
                165                 170                 175

Lys Ser Met Leu Met Gly Ser Ser Asp Ser Asp Asn Tyr Asn Arg Thr
            180                 185                 190

Ile Thr Phe His His Asn Trp Phe Glu Asn Leu Asn Ser Arg Val Pro
        195                 200                 205

Ser Phe Arg Phe Gly Glu Gly His Ile Tyr Asn Asn Tyr Phe Asn Lys
    210                 215                 220

Ile Ile Asp Ser Gly Ile Asn Ser Arg Met Gly Ala Arg Ile Arg Ile
225                 230                 235                 240

Glu Asn Asn Leu Phe Glu Asn Ala Lys Asp Pro Ile Val Ser Trp Tyr
                245                 250                 255

Ser Ser Ser Pro Gly Tyr Trp His Val Ser Asn Asn Lys Phe Val Asn
            260                 265                 270

Ser Arg Gly Ser Met Pro Thr Thr Ser Thr Thr Thr Tyr Asn Pro Pro
```

-continued

```
        275                 280                 285

Tyr Ser Tyr Ser Leu Asp Asn Val Asp Asn Val Lys Ser Ile Val Lys
    290                 295                 300

Gln Asn Ala Gly Val Gly Lys Ile Asn Pro
305                 310


<210> SEQ ID NO 25
<211> LENGTH: 416
<212> TYPE: PRT
<213> ORGANISM: Bacillus sp. TS-47

<400> SEQUENCE: 25

Lys Glu Leu Gly His Glu Val Leu Lys Pro Tyr Asp Gly Trp Ala Ala
1               5                   10                  15

Tyr Gly Glu Gly Thr Thr Gly Gly Ala Met Ala Ser Pro Gln Asn Val
            20                  25                  30

Phe Val Val Thr Asn Arg Thr Glu Leu Ile Gln Ala Leu Gly Gly Asn
        35                  40                  45

Asn His Thr Asn Gln Tyr Asn Ser Val Pro Lys Ile Ile Tyr Val Lys
    50                  55                  60

Gly Thr Ile Asp Leu Asn Val Asp Asp Asn Asn Gln Pro Val Gly Pro
65                  70                  75                  80

Asp Phe Tyr Lys Asp Pro His Phe Asp Phe Glu Ala Tyr Leu Arg Glu
                85                  90                  95

Tyr Asp Pro Ala Thr Trp Gly Lys Lys Glu Val Glu Gly Pro Leu Glu
            100                 105                 110

Glu Ala Arg Val Arg Ser Gln Lys Lys Gln Lys Asp Arg Ile Met Val
        115                 120                 125

Tyr Val Gly Ser Asn Thr Ser Ile Ile Gly Val Gly Lys Asp Ala Lys
    130                 135                 140

Ile Lys Gly Gly Gly Phe Leu Ile Lys Asn Val Asp Asn Val Ile Ile
145                 150                 155                 160

Arg Asn Ile Glu Phe Glu Ala Pro Leu Asp Tyr Phe Pro Glu Trp Asp
                165                 170                 175

Pro Thr Asp Gly Thr Leu Gly Glu Trp Asn Ser Glu Tyr Asp Ser Ile
            180                 185                 190

Ser Ile Glu Gly Ser Ser His Ile Trp Ile Asp His Asn Thr Phe Thr
        195                 200                 205

Asp Gly Asp His Pro Asp Arg Ser Leu Gly Thr Tyr Phe Gly Arg Pro
    210                 215                 220

Phe Gln Gln His Asp Gly Ala Leu Asp Ile Lys Asn Ser Ser Asp Phe
225                 230                 235                 240

Ile Thr Ile Ser Tyr Asn Val Phe Thr Asn His Asp Lys Val Thr Leu
                245                 250                 255

Ile Gly Ala Ser Asp Ser Arg Met Ala Asp Ser Gly His Leu Arg Val
            260                 265                 270

Thr Leu His His Asn Tyr Tyr Lys Asn Val Thr Gln Arg Leu Pro Arg
        275                 280                 285

Val Arg Phe Gly Gln Val His Ile Tyr Asn Asn Tyr Tyr Glu Phe Ser
    290                 295                 300

Asn Leu Ala Asp Tyr Asp Phe Gln Tyr Ala Trp Gly Val Gly Val Phe
305                 310                 315                 320

Ser Gln Ile Tyr Ala Gln Asn Asn Tyr Phe Ser Phe Asp Trp Asp Ile
                325                 330                 335

Asp Pro Ser Leu Ile Ile Lys Val Trp Ser Lys Asn Glu Glu Ser Met
```

-continued

```
            340                 345                 350

Tyr Glu Thr Gly Thr Ile Val Asp Leu Pro Asn Gly Arg Arg Tyr Ile
        355                 360                 365

Asp Leu Val Ala Ser Tyr Asn Glu Ser Asn Thr Leu Gln Leu Lys Lys
    370                 375                 380

Glu Val Thr Trp Lys Pro Met Phe Tyr His Val Ile His Pro Thr Pro
385                 390                 395                 400

Ser Val Pro Ala Leu Val Lys Ala Lys Ala Gly Ala Gly Asn Leu His
                405                 410                 415


<210> SEQ ID NO 26
<211> LENGTH: 341
<212> TYPE: PRT
<213> ORGANISM: Thermotoga maritima

<400> SEQUENCE: 26

Ala Ser Leu Asn Asp Lys Pro Val Gly Phe Ala Ser Val Pro Thr Ala
1               5                   10                  15

Asp Leu Pro Glu Gly Thr Val Gly Gly Leu Gly Gly Glu Ile Val Phe
            20                  25                  30

Val Arg Thr Ala Glu Glu Leu Glu Lys Tyr Thr Thr Ala Glu Gly Lys
        35                  40                  45

Tyr Val Ile Val Val Asp Gly Thr Ile Val Phe Glu Pro Lys Arg Glu
    50                  55                  60

Ile Lys Val Leu Ser Asp Lys Thr Ile Val Gly Ile Asn Asp Ala Lys
65                  70                  75                  80

Ile Val Gly Gly Gly Leu Val Ile Lys Asp Ala Gln Asn Val Ile Ile
                85                  90                  95

Arg Asn Ile His Phe Glu Gly Phe Tyr Met Glu Asp Asp Pro Arg Gly
            100                 105                 110

Lys Lys Tyr Asp Phe Asp Tyr Ile Asn Val Glu Asn Ser His His Ile
        115                 120                 125

Trp Ile Asp His Cys Thr Phe Val Asn Gly Asn Asp Gly Ala Val Asp
    130                 135                 140

Ile Lys Lys Tyr Ser Asn Tyr Ile Thr Val Ser Trp Cys Lys Phe Val
145                 150                 155                 160

Asp His Asp Lys Val Ser Leu Val Gly Ser Ser Asp Lys Glu Asp Pro
                165                 170                 175

Glu Gln Ala Gly Gln Ala Tyr Lys Val Thr Tyr His His Asn Tyr Phe
            180                 185                 190

Lys Asn Cys Ile Gln Arg Met Pro Arg Ile Arg Phe Gly Met Ala His
        195                 200                 205

Val Phe Asn Asn Phe Tyr Ser Met Gly Leu Arg Thr Gly Val Ser Gly
    210                 215                 220

Asn Val Phe Pro Ile Tyr Gly Val Ala Ser Ala Met Gly Ala Lys Val
225                 230                 235                 240

His Val Glu Gly Asn Tyr Phe Met Gly Tyr Gly Ala Val Met Ala Glu
                245                 250                 255

Ala Gly Ile Ala Phe Leu Pro Thr Arg Ile Met Gly Pro Val Glu Gly
            260                 265                 270

Tyr Leu Thr Leu Gly Glu Gly Asp Ala Lys Asn Glu Phe Tyr Tyr Cys
        275                 280                 285
```

-continued

```
Lys Glu Pro Glu Val Arg Pro Val Glu Glu Gly Lys Pro Ala Leu Asp
    290                 295                 300

Pro Arg Glu Tyr Tyr Asp Tyr Thr Leu Asp Pro Val Gln Asp Val Pro
305                 310                 315                 320

Lys Ile Val Val Asp Gly Ala Gly Ala Gly Lys Leu Val Phe Glu Glu
                325                 330                 335

Leu Asn Thr Ala Gln
            340
```

PECTATE LYASES WITH INCREASED THERMOSTABILITY AND/OR ENZYMATIC ACTIVITY

CROSS-REFERENCE TO RELATED APPLICATIONS

This application is a national entry of International Patent Application PCT/CA2008/000867 filed May 5, 2008 and claims the benefit of U.S. Provisional Patent Application Ser. No. 60/924,386 filed May 11, 2007, the entire contents of both of which is are herein incorporated by reference.

FIELD OF THE INVENTION

The present invention is directed to pectate lyases, in particular to genetically modified pectate lyases having increased thermostability and/or enzymatic activity. Such pectate lyases are useful in detergents and in bioscouring.

BACKGROUND OF THE INVENTION

Extraction of fiber from fiber plants would allow its eventual usage. Extraction primarily involves removal of non-cellulosic material, e.g. pectin and colour-containing materials, from the fiber. This removal of non-cellulosic material is sometimes referred to as degumming. Pectin is a polysaccharide which is a polymer of galacturonic acid. Pectin is not soluble in water or acid. However, it can be removed by strong alkaline solutions like caustic soda (concentrated sodium hydroxide).

General methods for isolation of clean fibers include dew retting, water retting, and chemical and enzymatic processes, with different variations. In these methods, the glue that holds the fibers together must first be loosened (or removed altogether) by retting. In conventional retting, stalks are dew-retted by allowing them to lie in the field after cutting. These retting approaches depend on digestion of pectin by enzymes secreted by microbes thriving under favorable conditions. Although water-retting yields more uniform fiber, the process pollutes the water. Dew-retting requires anywhere from two to six weeks or more to complete, requiring the stalks to be turned at least once for highest-quality fiber. Dew-retting is thus affected by the weather, which offers no guaranty of favorable condition.

On an industrial scale, chemical scouring is common. Chemical scouring is a process that improves the water absorbancy and the whiteness of textile by removing the non-cellulosic substances from cotton, flax or other natural cellulosic fibers, thereby facilitating the subsequent dyeing and finishing processes (Sawada and Ueda. 2001; Solbak, et al. 2005; Tzanov et al., 2001). Violent, hazardous chemicals like soda ash, caustic soda and oxalic acid used in the current scouring processes cause severe environmental problems, besides a loss of fiber strength.

In the past several years, considerable attention has been paid to replacing traditional processes, e.g. chemical scouring of raw cotton and flax fabrics and retting of flax and hemp fibers, with more environmentally friendly and economically viable biotechnological processes. Enzyme retting or bioscouring involves the action of a pectinase, especially pectate lyase, with or without other enzymes like xylanase and/or cellulase. Such processes are generally known (Akin et al., 2001; Klug-Santner et al., 2006; Ossola and Galante. 2004; Ouajai and Shanks. 2005; Sawada and Ueda. 2001; Solbak, et al. 2005; Tzanov et al., 2001). Pectate lyases specifically remove non-cellulosic material without damaging the cellulose backbone of the fiber. Further, enzymes used for bioscouring reduce environmental pollution (Solbak, et al. 2005). Pectate lyases widely exist in bacteria (Berensmeier et al. 2004; Klug-Santner, et al. 2006; Kluskens, et al. 2003) and fungi (Benen et al. 2000; Huertas-Gonzalez et al. 1999).

Other examples of prior art include U.S. Pat. No. 6,124,127, WO 2001/079440, WO 2000/042152 and WO 2006/0089283. These documents disclose various pectate lyases for use in detergents or textile processing.

Despite the interest in pectate lyases for use in bioscouring processes, many pectate lyases currently in use suffer from a lack of scouring efficiency. Lack of scouring efficiency can arise from thermal instability and/or low enzymatic activity of the pectate lyase. Thermal instability results in reduction of activity over time due to thermally induced changes in enzyme conformation. Higher temperatures accelerate reduction in activity. Low enzymatic activity limits the rate at which scouring can occur. Scouring efficiency can be increased by using pectate lyases having increased thermostability and/or enzymatic activity.

Thus, there is a need for enzymes, particularly pectate lyases, having increased thermostability and/or enzymatic activity.

SUMMARY OF THE INVENTION

It has now been found that certain variants of a *Xanthomonas campestris* pectate lyase have improved thermostability, enzymatic activity or both thermostability and enzymatic activity.

Thus, there is provided a polypeptide comprising the amino acid sequence (SEQ ID NO: 2):

MTSKTLQGALALALSACAAGAIAGPVGYGA$X_1$TTGGGNKVPVNVATFEAM

QSAIDSYSGSGGLVLNYTGKFDFGTIKDVCAQWKLPAKTVQIKNKSDVTI

KGANGSAANFGIRVVGNAHNVIIQNMTIGLLQGGEDADSISLEGNSSGEP

SKIWVDHNTVFASLTKCSGAGDASFDGGIDMKKGVHHVTVSYNYVYNYQK

VALNGYSDSDTKNSAARTTYHHNRFENVESRVPLQR$X_2$GLSHIYNNYFNN

VTTSGINVRMGGIAKIESNYFENIKNPVTSRDSSEIGYWDLINNYVGSGI

TWGTPDGSKPYANATNWISTKVFPESLGYIYTVTPAAQVKAKVIATAGAG

KNLAE wherein $X_1$ is alanine or glycine and $X_2$ is arginine or phenylalanine with the proviso that $X_2$ is not arginine when $X_1$ is alanine.

There is also provided a process of isolating fibers from non-cellulosic material in a fiber plant comprising contacting raw fibers of the fiber plant with a polypeptide of the present invention.

Polypeptides of the present invention are enzymes and are variants of *Xanthomonas campestris* pectate lyase II (XcPL). Individual variants include polypeptides having an amino acid sequence of SEQ ID NO: 3, SEQ ID NO: 4 or SEQ ID NO: 5.

Enzymes of the present invention are stable in a pH range of 4-10, and function optimally at a pH of about 8.5. They advantageously possess improved thermostability, enzymatic activity or both thermostability and enzymatic activity, in comparison to the wild-type *X. campestris* pectate lyase. Thermostability may be at least two times greater, for example at least ten times greater, and in some embodiments at least twelve times greater and in other embodiments at least twenty three times greater, than that of the wild-type enzyme. Enzymatic activity may be at least two times greater, and in some embodiments at least five times greater, than that of the wild-type enzyme. Half-life of enzymatic activity at 45° C. for enzymes of the present invention may be 3 hours or more, or even 10 hours or more.

Enzymes of the present invention may be used in detergents for degrading non-cellulosic material, for degrading non-cellulosic material in textile processing, for degrading non-cellulosic material in cellulose fiber processing, for degrading non-cellulosic material in the treatment of pectic wastewaters, for degrading non-cellulosic material in paper making, for degrading non-cellulosic material in coffee and tea fermentations and for improving the yield and the clarification of fruit juices. They are particularly useful as a detergent for the treatment of cellulosic material, especially cellulose-containing fibers, yarn, woven or non-woven fabric, and treatment of mechanical paper-making pulps or recycled waste paper, and as a bioscouring agent for retting of fibers. The enzymes of the invention are very effective for use in an enzymatic scouring process in the preparation of cellulosic material e.g. for proper response in subsequent dyeing operations. Further, it is contemplated that detergent compositions comprising the novel enzymes are capable of removing or bleaching stains present on laundry, especially stains resulting from galactan or arabinogalactan containing food, plants, and the like. Treatment with detergent compositions comprising an enzyme of the present invention can prevent binding of certain stains to the cellulosic material.

Bioscouring (enzymatic retting) involves enzymatic removal of non-cellulosic material, especially pectin, from raw plant fibers, for example hemp, jute, flax, ramie and cotton. In accordance with the present invention, enzymatic treatment of raw fibers employs one or more enzymes of the present invention. One or more other enzymes may also be used, for example, proteases, cellulases (endoglucanases), beta-glucanases, hemicellulases, lipases, peroxidases, laccases, alpha-amylases, glucoamylases, cutinases, pectinases, reductases, oxidases, phenoloxidases, ligninases, pullulanases, arabinosidases, mannanases, xyloglucanases, xylanases, pectin acetyl esterases, polygalacturonases, rhamnogalacturonases, galactanases, pectin lyases, other pectate lyases, polygalacturonases, pectin methylesterases, cellobiohydrolases, transglutaminases or mixtures thereof.

Preferably, enzymatic treatment is performed in an aqueous medium at a pH of from about 4-10. More preferably, the pH is from about 8-9. Preferably, the temperature at which enzymatic treatment is performed is in a range of from about 30° C. to 55° C., for example in a range of from about 40° C. to 50° C. Preferably, the aqueous medium contains salts and/or buffers, for example monosodium citrate. Concentration of any salts or buffers should not be too high as to unduly affect activity of the enzyme. For example, the concentration of monosodium citrate may be in a range of about 3-7 mM, e.g. 5 mM.

Preferably, enzymatic treatment of the fibers is performed for a period of time in a range of from about 0.5-10 hours, for example about 1-6 hours. In some embodiments, 1-3 hour of treatment is sufficient. Stirring or agitation of the aqueous medium may be done. Preferably, the aqueous medium is stirred or agitated constantly during enzymatic treatment. Purified fiber after enzymatic treatment may be rinsed with water.

Specific conditions under which the enzymatic treatment is conducted may depend on various factors, for example the nature and amount of raw fiber being treated, and the use to which the fiber is ultimately destined.

In common fiber plants a bark-like layer containing bast fibers surrounds a woody core. Before enzymatic treatment can be performed on the bast fibers, it may be necessary to remove the woody core. Decortication, either manually or mechanically, is a process that separates the bark-like layer from the woody core.

Enzymatic treatment of raw fibers may be used in conjunction with other treatment steps, for example chemical scouring. Purified fiber may be subjected to other treatment steps, for example bleaching, dyeing, etc., for its eventual application. Enzymatic treatment advantageously reduces the amount of violent and hazardous chemicals required in the other treatment steps.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1 depicts multiple alignment of amino acid sequences of thermostable pectate lyases from *Bacillus licheniformis, Bacillus* sp. TS-47 and *Thermotoga maritima* and a thermoliable pectate lyase from *Xanthomonas campestris* (*X. campestris* pectate lyase II);

FIG. 2 depicts amino acid sequences of parent *Xanthomonas campestris* pectate lyase II and three of its variants (mutants A31G, R236F and A31G/R236F);

DESCRIPTION OF PREFERRED EMBODIMENTS

Figure 3A:
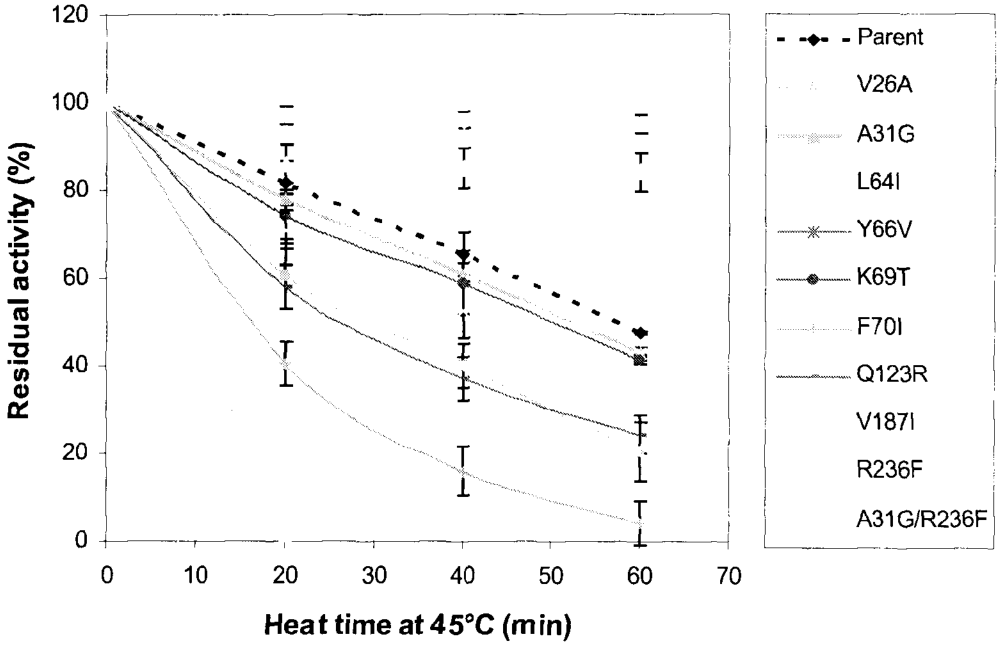
FIG. 3 depicts graphs illustrating thermostability of parent *Xanthomonas campestris* pectate lyase II and its variants, including mutants A31G, R236F and A31G/R236F.

The term "wild-type enzyme" denotes an enzyme, which is endogenous to a naturally occurring microorganism found in nature.

The term "parent enzyme" means an enzyme in which modifications are being made to produce enzyme variants. A parent enzyme may be an enzyme isolated from a natural source, or an enzyme wherein previous modification(s) have been made while retaining the characteristic activity of the enzyme in question. The parent pectate lyase may be wild-type pectate lyase.

Materials and Methods

Multiple sequence alignment. Three thermostable pectate lyases: CAD56882 from *Bacillus licheniformis* (Berensmeier et al. 2004), BAB40336 from *Bacillus* sp. TS-47 (Takao et al. 2001), AAD35518 from *Thermotoga maritima* MSB8 (Kluskens, et al. 2003) with optimal temperatures of 65° C., 70° C. and 90° C., respectively and *Xanthomonas campestris* pectate lyase II (NP_638163) (da Silva et al. 2002), a mesophilic protein with optimal temperature of 50° C. established in this study, were analyzed by multiple sequence alignment using the European Molecular Biology Laboratory—European Bioinformatics Institute (EMBL-EBI) ClustalW program. Protein sequences in this alignment are indicated by their accession numbers in the NCBI protein database. Not shown are the putative signal peptide sequences of the respective proteins.

Site-directed mutagenesis. Site-directed mutagenesis was performed by using the QuikChange® Mutagenesis kit (Stratagene, La Jolla, Calif.) according to its instruction manual. The mutagenic oligonucleotide primers are listed in Table 1. The expected mutations were confirmed by gene sequencing using a Big Dye DNA sequencing kit (Applied Biosystems) with an automated DNA sequencer (Model 377, ABI Prism).

Molecular cloning techniques. Standard methods were used for isolation of plasmid DNA, cloning and transformation (Sambrook et al. 1989). The *Xanthomonas campestris* pectate lyase II gene was cloned into an IPTG-inducible bacterial-expression vector, pSD80 (Smith et al. 1996), at the EcoRI and HindIII restriction sites. The recombinant plasmids containing the parent and mutated *X. campestris* pectate lyase gene fragments were separately transformed into the Rosetta pRARE strain, *Escherichia coli* BL21 (DE3) (Novagen).

Protein expression. Single colonies harboring *Xanthomonas campestris* pectate lyase II gene with desired mutations were grown at 37° C. on a rotary shaker of 250 rpm in 5 ml of LB medium containing 50 μg/ml ampicillin and 30 μg/ml chloramphenicol. The overnight cultures were diluted 200 fold into the same fresh LB medium, grown to $OD_{600}$≅0.4 to 0.5 under the same culture conditions, and then induced with 1 mM IPTG for 3 hours. The bacterial cells were precipitated and disrupted by French Press. The clear supernatant of cell lysate was used for enzymatic assay after centrifugation at 14000 rpm for 40 min at 4° C.

Protein purification. The supernatant of cell lysate was loaded on to a HiPrep™ 16/10 SP XL column (Amersham Pharmacia). The active peak detected by pectate lyase assay (Collmer et al. 1988) was eluted with a linear NaCl gradient from 0 to 200 mM in 20 mM sodium phosphate buffer, pH 7. Protein concentration was determined by Bradford assay (Bradford 1976).

Gel electrophoresis and zymogram staining. 200 ng of protein samples were heated for 10 min at 45° C. in sample loading buffer before being applied to 10% SDS-PAGE containing 0.1% polygalacturonic acid. After electrophoresis, protein bands were stained with Coomassie Blue. For zymogram staining, the gel was soaked in 2.5% Triton™ X-100 for 30 min, washed with 50 mM Tris-HCl pH 8.5 containing 0.5 mM $CaCl_2$ for 30 min. After 20 h of incubation at 40° C. in 50 mM Tris-HCl pH 8.5 containing 0.5 mM $CaCl_2$ and 0.1% polygalacturonic acid, the gel was stained with 0.05% (w/v) ruthenium red for 20 min and washed with water for 60 min.

Pectate lyase assay. The pectate lyase activity was determined by measuring the increase in absorbance at 232 nm of polygalacturonic acid (PGA) (Collmer et al. 1988). 50 μl of enzyme and 50 μl of 0.5% PGA in 50 mM Tris-HCl pH 8.5 containing 0.5 mM $CaCl_2$ were incubated at 50° C. for 30 min. The reaction was stopped with addition of 20 μl of 0.35 M HCl. 100 μl of reaction mixture was used to determine the absorbance at 232 nm. One unit (IU) of pectate lyase was defined as the enzyme amount producing 1 μmol of unsaturated product in 1 min under the assay conditions. The molar

TABLE 1

| Mutant | Direction | SEQ ID | Nucleotide sequence |
|---|---|---|---|
| V26A | Forward | NO: 6 | 5'-GATCGCAGGTCCGGCCGGCTACGGTG-3' |
| | Reverse | NO: 7 | 5'-CACCGTAGCCGGCCGGACCTGCGATC-3' |
| A31G | Forward | NO: 8 | 5'-GCTACGGTGCCGGCACCACCGGCG-3' |
| | Reverse | NO: 9 | 5'-CGCCGGTGGTGCCGGCACCGTAGC-3' |
| L64I | Forward | NO: 10 | 5'-CGGCGGCCTGGTGATCAACTACACCGGCAAG-3' |
| | Reverse | NO: 11 | 5'-CTTGCCGGTGTAGTTGATCACCAGGCCGCCG-3' |
| Y66V | Forward | NO: 12 | 5'-GCCTGGTGCTGAACGTCACCGGCAAGTTCGACTTC-3' |
| | Reverse | NO: 13 | 5'-GAAGTCGAACTTGCCGGTGACGTTCAGCACCAGGC-3' |
| K69T | Forward | NO: 14 | 5'-CTGAACTACACCGGCACGTTCGACTTCGGC-3' |
| | Reverse | NO: 15 | 5'-GCCGAAGTCGAACGTGCCGGTGTAGTTCAG-3' |
| F70I | Forward | NO: 16 | 5'-GAACTACACCGGCAAGATCGACTTCGGCACC-3' |
| | Reverse | NO: 17 | 5'-GGTGCCGAAGTCGATCTTGCCGGTGTAGTTC-3' |
| Q123R | Forward | NO: 18 | 5'-GCACAACGTGATCATCCGGAACATGACCATCGG-3' |
| | Reverse | NO: 19 | 5'-CCGATGGTCATGTTCCGGATGATCACGTTGTGC-3' |
| V187I | Forward | NO: 20 | 5'-GGCGTGCATCACATCACCGTGTCCTACAAC-3' |
| | Reverse | NO: 21 | 5'-GTTGTAGGACACGGTGATGTGATGCACGCC-3' |
| R236F | Forward | NO: 22 | 5'-CCGCTGCAGCGCTTTGGCTTGAGCCACATC-3' |
| | Reverse | NO: 23 | 5'-GATGTGGCTCAAGCCAAAGCGCTGCAGCGG-3' |

extinction coefficient for the unsaturated product at 232 nm is 4600 $M^{-1}$ $cm^{-1}$. All data were average of the triplicate measurements. Kinetic parameters $K_m$, $V_{max}$, $K_{cat}$ were determined at the optimal temperature of each selected purified enzymes.

Thermostability measurement. To determine the half-life of inactivation, the pectate lyases were incubated in 50 mM Tris-HCl buffer pH 8.5 containing 0.5 mM $CaCl_2$ at 45° C. Samples were taken at various time points and followed by the pectate lyase assay. Purified proteins were adjusted to about 0.5 mg/ml in 10 mM phosphate buffer, pH 7.0 for determining the Circular Dichroism (CD) spectrum and melting temperature. Thermal denaturation experiments were performed at 40° C. of temperature increase per hour. The data were collected with JASCO J-710 CD spectrometer at the wavelength of 222 nm, where maximal signal difference was observed.

Protein crystallization and structure determination. Initial crystallization conditions were identified using the Pegs (Nextal, Montreal), Classic Suite I and II (Qiagen) screens, with the sitting drop vapor diffusion set-up at 20° C. Numerous chemical conditions yielded triclinic crystals overnight. The conditions were reproduced and optimized using the hanging drop vapor diffusion method in 24-well Linbro plates (Hampton Research). The best conditions found were 20-30% (w/v) PEG 3350, and various buffers with pH ranging from 5.5 to 8.5. The crystals belong to the primitive triclinic space group P1, with the unit cell dimensions of a=47.2 Å, b=53.2 Å, c=73.0 Å, α=71.7°, β=80.0°, γ=69.0°, and two protein molecules in the asymmetric unit. The Matthews coefficient $V_M$ is 2.20 $Å^3$ $Da^{-1}$, corresponding to a solvent content of 44%. The cryoprotectant solution used consisted of mother liquor supplemented with 10-12% (w/v) glycerol and data were collected at 100K. Diffraction data extending to 2, 2.1, 1.9 Å resolution for wild-type, R236F, A31G/R236G proteins, respectively. The images were processed with the HKL2000 program package. The structure of wild-type XcPL was solved by molecular replacement using the MolRep program and the structure of *E. chrysanthemi* pectate lyase (PDB entry 1AIR) as a search model. Free atom density modification was implemented using ARP/wARP to improve the electron density maps, and the protein model was built manually using COOT. The model was refined using REFMAC5 with the TLS option with each of the monomers treated separately. The structures of R236F and A31G/R236F mutants was solved and refined in the same manner as wild-type XcPL whose structure was used as a search model for molecular replacement. Refinement statistics are summarized in Table 5 for the three structures solved. The models were validated with PROCHECK. Coordinates have been deposited in the Protein Data Bank with the codes 2OX3, 2OXZ, 2OY1 corresponding to wild-type, R236F and A31G/R236F, respectively.

Computational method. The stabilities (i.e., the free energies of folding) of pectate lyase mutants relative to the wild type protein were calculated with the FOLD-X program, using the crystal structure of the wild type protein determined in this study (chain A). The FOLD-X program employs a first principle-based energy function that was shown to be able to predict folding free energies with a squared-correlation coefficient of 0.69 and a standard deviation of 0.81 kcal/mol, within a dataset of over 1000 mutations from various proteins. The effect of R236F mutation on stability was further verified by performing a FOLD-X calculation using the crystal structure of the R236F mutant (chain A) and simulating its mutation to the wild-type protein. All crystallographic water molecules and observed phosphate ions were removed. Possible water bridges between protein atoms were implicitly taken into account during FOLD-X calculations. Point mutations were introduced by the FOLD-X program with the mutate function of the WHAT IF program that optimizes the mutated side-chains with respect to rotamer distributions and hydrogen-bond networking. The analysis of relative stabilities in terms of contributions from van der Waals, hydrogen bonding, electrostatic and water bridge interaction energies, hydrophobic and polar desolvation, and main-chain and side-chain entropies, were based on the FOLD-X calculations. Clash energies were not included in the calculation of folding free energies.

RESULTS

Example 1

Characterization of the Properties of *Xanthomonas campestris* Pectate Lyase II (XcPL)

The full-length XcPL gene encodes a polypeptide having 353 amino acids, with a molecular weight of 37 kD and pl of 8.7 according to its DNA-predicted amino acid sequences. Optimal pH and temperature of the enzyme were found to be 8.5 and 50° C., respectively. Melting temperature of this enzyme was determined to be 48° C. Half-life of inactivation at 45° C. for this enzyme was determined to be 54 min.

Example 2

Selecting Mutations on the XcPL Polypeptide

Three thermostable pectate lyases, which have been biochemically characterized: CAD56882 from *Bacillus licheniformis*, BAB40336 from *Bacillus* sp. TS-47, AAD35518 from *Thermotoga maritima* MSB8 and thermoliable XcPL (NP_638163) were analyzed by multiple sequence alignment using ClustalW program. Compared with XcPL pairwisely, the thermostable pectate lyases share only 25-35% of identical amino acids. Interestingly, 9 amino acid residues in underlined font without bolding in FIG. 1 (corresponding to positions 26, 31, 64, 66, 69, 70, 123, 187 and 236 of the wild-type XcPL (NP_638163)) were found to be highly conserved in all three thermostable pectate lyases, but variable in the thermoliable XcPL (FIG. 1). Residues in bold font without underlining in FIG. 1 are conserved catalytic sites, residues in underlined bold italic font in FIG. 1 are conserved calcium binding sites, the gray shaded region in FIG. 1 is the core structure of the parallel β-helix vWiDH region, and residues in underlined font without bolding in FIG. 1 are sites conserved in the thermostable pectate lyases (CAD56882 from *Bacillus licheniformis*, BAB40336 from *Bacillus* sp. TS-47, AAD35518 from *Thermotoga maritima* MSB8) but variant in *Xanthomonas campestris* pectate lyase II (NP_638163).

Example 3

Effect of Single Amino Acid Substitution and a Double Mutation on the Thermostability of XcPL Individual effects of amino acid substitutions in an enzyme are generally difficult to predict. Enzyme properties may be unaffected, adversely affected or positively affected. To determine the individual effect of each of the conserved amino acids in thermostable pectate lyases on the thermostability of XcPL, nine mutants of the *Xanthomonas campestris* pectate lyase II enzyme were produced, each containing a single substitution with conserved amino acid at a position corresponding to one of the nine sequence differences between the three thermostable pectate lyases and the thermoliable one.

Referring to Tables 1 and 2, in the name of each mutant the number refers to the amino acid position in the parent enzyme, the first letter refers to the amino acid present at that position in the parent and the second letter refers to the amino acid present at that position in the mutant.

TABLE 2

| Enzyme | Half-life of inactivation at 45° C. (min) | Activity in crude cell extract (IU/mg protein) |
|---|---|---|
| Parent | 54.2 ± 5.9 | 0.64 ± 0.01 |
| V26A | 38.8 ± 8.5 | 0.53 ± 0.04 |
| A31G | 51.9 ± 8.8 | 3.37 ± 0.09 (5×) |
| L64I | 44.6 ± 2.8 | 0.54 ± 0.01 |
| Y66V | NA | No activity |
| K69T | 48.2 ± 7.4 | 0.87 ± 0.03 |
| F70I | 14.0 ± 1.5 | 0.81 ± 0.03 |
| Q123R | 29.0 ± 1.3 | 0.62 ± 0.08 |
| V187I | <10 | 0.55 ± 0.08 |
| R236F | 1292 ± 139 (23×) | 1.42 ± 0.17 (2×) |
| A31G/R236F | 659 ± 41 (12×) | 3.48 ± 0.20 (5×) |

FIG. 2 provides the amino acid sequences of the parent (wild-type) *Xanthomonas campestris* pectate lyase II (SEQ ID NO: 1) and three of its mutants: A31G (SEQ ID NO: 3), R236F (SEQ ID NO: 4) and A31G/R236F (SEQ ID NO: 5). The amino acid sites that are modified in the mutants are in underlined bold font. Thus, alanine at position 31 in the parent enzyme is converted to glycine in mutants A31G and A31G/R236F. Arginine at position 236 in the parent enzyme is converted to phenylalanine in mutants R236F and A31G/R236F.

Figure 3B:
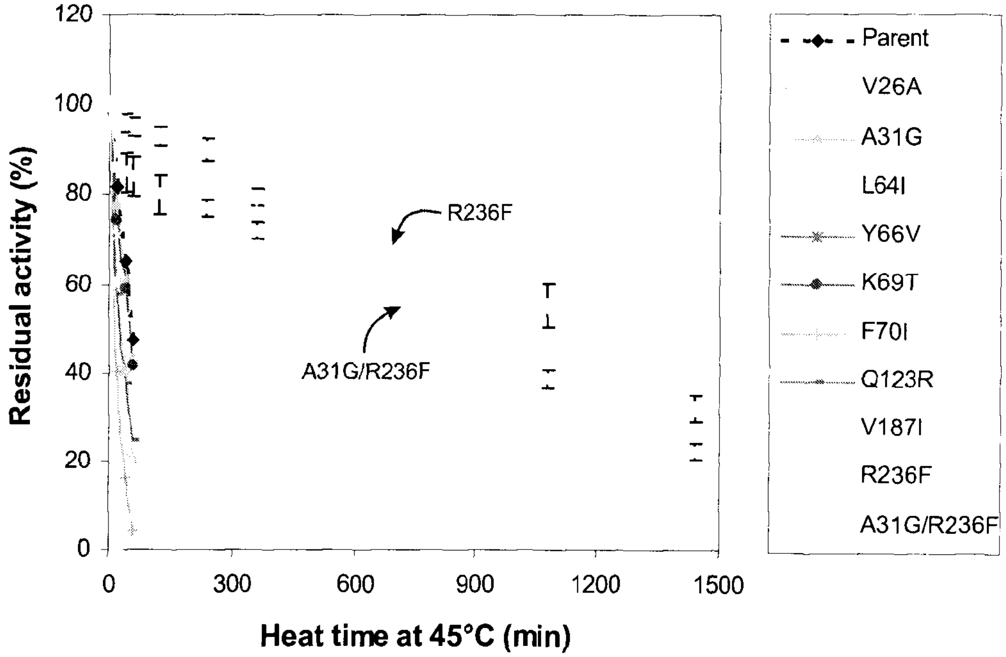

One of the single mutants, Y66V, exhibited no enzymatic activity. Four out of nine individual single mutants, F70I, Q123R, V187I and R236F exhibited a remarkable difference in thermostability when compared to the parent enzyme. F70I, Q123R and V187I had remarkably lower thermostability while R236F had remarkably higher thermostability. Notably, the mutant R236F displayed 23 times longer half-life at 45° C. than the parent. In addition, the mutant A31G was 5-fold more active than the parent while its thermostabilty remained similar to the parent. The most active mutant A31G and the most thermostable mutant R236F were combined to produce a double mutant A31G/R236F. This resulted in 5 times more activity and 12 times more thermostability than the parent enzyme (Table 2 and FIG. 3). In Table 2, the numbers in parentheses are fold of improved properties over the parent. It can be seen from Table 2 and FIG. 3 that the stability of wild-type *Xanthomonas campestris* pectate lyase is low. Its half-life of inactivation at 45° C. is less than one hour. About 90% of the original activity was lost after 3 hours at 45° C.

Example 4

Kinetic Properties of the Improved Mutant Pectate Lyases

Figure 4:
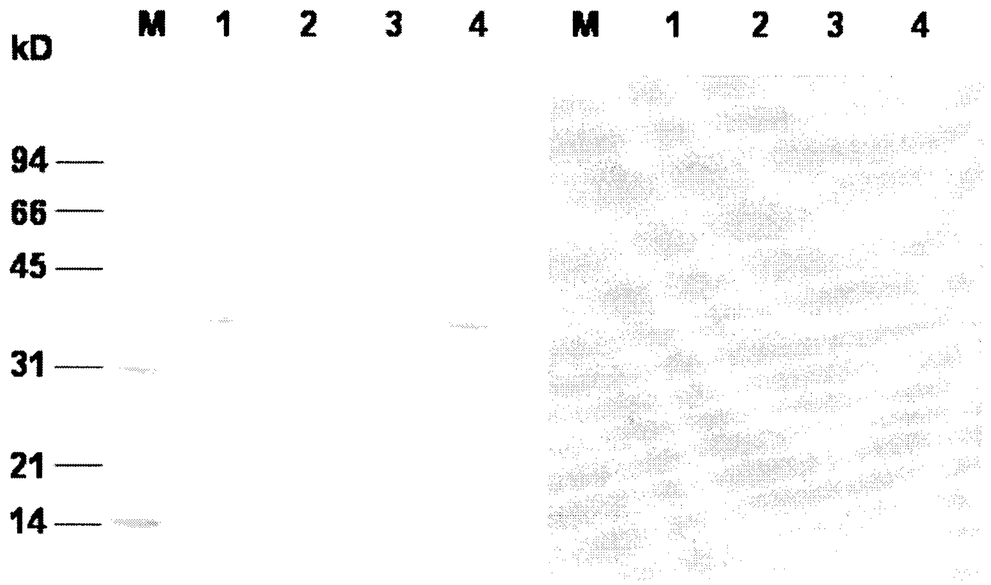
FIG. 4 depicts (left) SDS-PAGE analysis (Coomassie blue stained 10% SDS-PAGE) and (right) a zymogram (SDS-PAGE containing 0.1% PGA stained with ruthenium red) of purified expressed proteins of parent *Xanthomonas campestris* pectate lyase II and its mutants, in which Lane M=Molecular standard, Lane 1=parent pectate lyase, Lane 2=mutant A31G, Lane 3=mutant R236F, and Lane 4=mutant A31G/R236F.

To confirm the enzyme properties of the improved mutants derived from *Xanthomonas campestris* pectate lyase II, three mutant enzymes A31G, R236F and double mutant A31G/R236F and the parent enzyme were purified to apparent homogeneity with a single cation-exchange SP-Sepharose column. Those peaks appeared as a single band on SDS-PAGE with a molecular mass of 37 kD, in good agreement with their theoretical molecular weight (37,355 daltons). Furthermore, zymogram analysis of the purified enzymes indicated these single bands were active pectate lyases. The intensity of the clearing band for each enzyme is consistent with its specific activity (FIG. 4). The $K_m$ values of the mutants A31G, R236F and A31G/R236F using polygalacturonic acid (PGA) as substrate are not significantly different from each other and to the parent enzyme. However, the catalytic efficiency for both single mutant A31G and double mutant A31G/R236F increased about 2-fold, compared to parent enzyme. The activity for the most thermostable mutant R236F still retained the same level of its parent. The specific activities of the purified enzymes are consistent with their $K_{cat}/K_m$ values (Table 3). Similar results were observed when citrus pectin was used as the substrate (Table 4). Comparing the specific activities of the activities in crude cell extract and the purified enzymes (Table 2 and Table 3), the protein expression levels in strains harboring A31G, R236F and A31G/R236F mutant XcPL genes were 2 to 3 fold greater than on the strain harboring the wild-type gene.

TABLE 3

| Enzyme | $K_m$ ($g \cdot l^{-1}$) | $K_{cat}$ ($s^{-1}$) | $K_{cat}/K_m$ ($l \cdot g^{-1} \cdot s^{-1}$) | Specific activity (IU/mg) |
|---|---|---|---|---|
| Parent | 0.98 | 114 | 116 | 196 |
| A31G | 0.73 | 194 | 266 | 333 |
| R236F | 0.83 | 121 | 146 | 208 |
| A31G/R236F | 0.93 | 216 | 232 | 370 |

TABLE 4

| Enzyme | $K_m$ ($g \cdot l^{-1}$) | $K_{cat}$ ($s^{-1}$) | $K_{cat}/K_m$ ($l \cdot g^{-1} \cdot s^{-1}$) | Specific activity (IU/mg) |
|---|---|---|---|---|
| Parent | 0.80 | 61 | 76 | 105 |
| A31G | 0.68 | 117 | 172 | 200 |
| R236F | 0.59 | 67 | 114 | 115 |
| A31G/R236F | 0.55 | 139 | 253 | 238 |

Example 5

Determination of Melting Temperatures of Mutant Pectate Lyases

Figure 5:
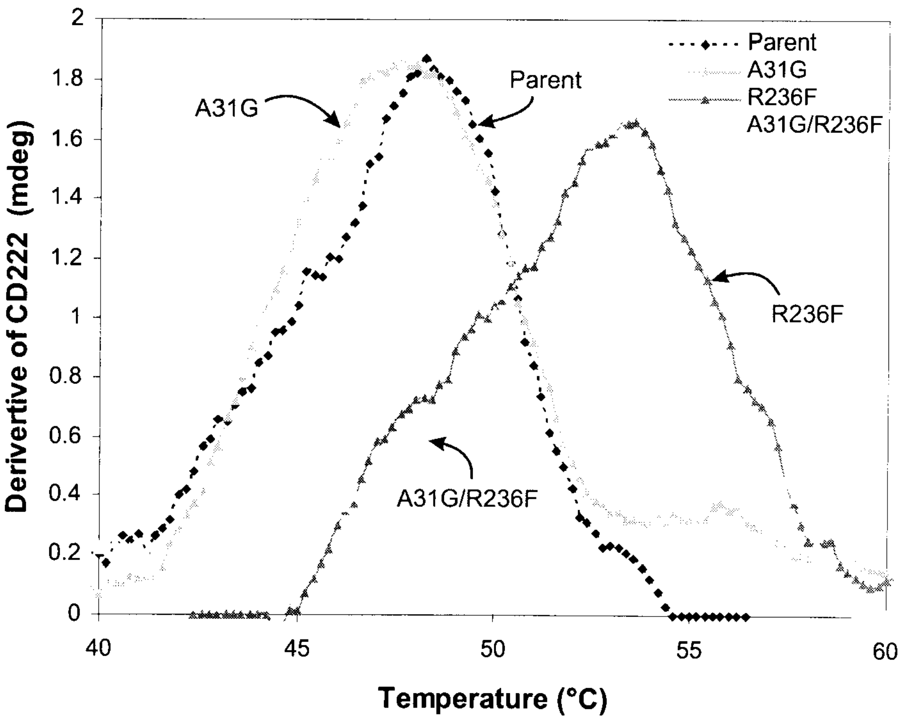
FIG. 5 depicts a graph of melting temperatures of parent *Xanthomonas campestris* pectate lyase II and its mutants A31G, R236F and A31G/R236F; and, FIG. 6 depicts a graph of the effects of parent *Xanthomonas campestris* pectate lyase II and its mutants A31G, R236F and A31G/R236F on release of pectin from natural hemp fiber.

The melting temperatures of purified parent enzyme, mutant A31G, mutant R236F and mutant A31G/R236F were determined by circular dichroism spectrometry to be 48° C., 47.5° C., 54° C. and 53° C., respectively (FIG. 5), which are consistent with their half-lives at 45° C. (Table 2).

Example 6

Effect of Mutants on Efficiency of Pectin Removal from Hemp Fiber

The amount of 4,5-unsaturated galacturonate residues liberated from pectin, which is measured by the increasing absorbance at 232 nm (Collmer et al. 1988), was used as an indicator for the effect of pectate lyase on the removal of pectic substance from untreated hemp fibers (Ouajai and Shanks. 2005). The amount of pectin-degraded products was confirmed with dinitrosalicylic acid assay (Miller. 1959). In this study, to determine the efficiency of the improved *Xan-*

Figure 6:
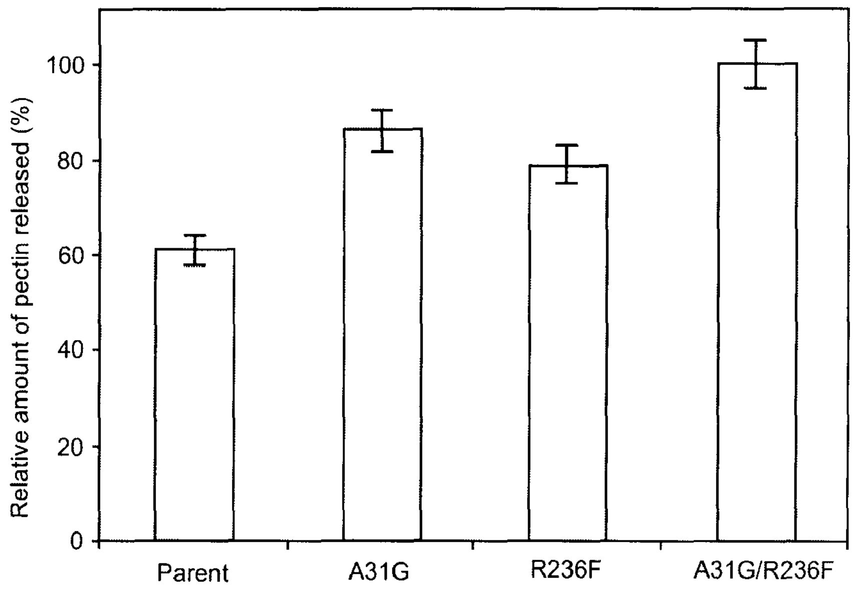

*thomonas campestris* pectate lyase variants in the bioscouring process, XcPL mutants A31G, R236F and A31G/R236F were used to treat natural hemp fiber with parent (wild-type) XcPL used as a control. All three of the mutants were found to be more effective in removing pectin from hemp fiber than the parent (FIG. 6). Setting release of pectin by the action of the double mutant A31G/R236F at 100%, the parent XcPL resulted in a pectin release of about 60% while mutants A31G and R236F resulted in pectin releases of about 85% and 80%, respectively.

Example 7

Structural Analysis of Wild-Type XcPL and Mutant Proteins

To understand the structural basis for thermal stability of the mutant proteins, R236F, A31G/R236F and wild-type XcPL were crystallized and their structures solved by molecular replacements. These structures share the same right-handed parallel β-helix architecture as described for *Erwinia chrysanthemi* (now classified as *Dickeya dadantii*) pectate lyase PelC. Crystallographic data collection and refinement is shown in Table 5.

TABLE 5

| | Wild-type | R326F | A31G/R236F |
|---|---|---|---|
| Data Collection | | | |
| Resolution range | 69.17-2 | 69.5-2.1 | 69.3-1.9 |
| Unique reflections | 33827 | 29174 | 42284 |
| Completeness (%) | 83.29 | 85.3 | 89.08 |
| Rsym[a] | 0.048 | 0.047 | 0.059 |
| Average I/σ(I) | 20.1 | 22 | 28.3 |
| Refinement Statistics | | | |
| Rwork[b] | 15.7 | 15.9 | 16.1 |
| Rfree[b] | 21.1 | 26.4 | 18.9 |
| Ramachandran plot | | | |
| Allowed (%) | 98.9 | 99.1 | 99.1 |
| Generously allowed (%) | 1.1 | 0.9 | 0.9 |
| r.m.s. Deviation | | | |
| Bonds (Å) | 0.01 | 0.009 | 0.006 |
| Angles (°) | 1.283 | 1.180 | 1.062 |

[a]Rsym = (Σ | Iobs − Iavg|)/Σ Iavg

[b]Rwork/free = (Σ | Fobs − Fcalc|)/Σ Fobs

Residue R236 is partially solvent-exposed and located in the T1.6 loop (the 6th loop of turn T1) that confers catalytic activity to the 8-helix core. Its guanidinium group is 10 Å, 17 Å and 22 Å away from the putative active sites R235, R230 and K199, respectively. This may explain the similar activities of wild-type and R236 mutant enzymes. The R236F substitution caused no structural change in the enzyme. Although bulkier, the F236 side chain occupies the same region of space as the wild-type R236; no neighboring residues were affected nor major electrostatic interactions interrupted. However, the aromatic side chain in this position allows hydrophobic interactions with several adjacent side chains, particularly M258 from the T1.7 loop, the aliphatic portions of T210 and N212 from the T1.5 loop, and the neighboring R235. Hydrophobic stacking between the T1.5 and T1.7 loops appears to confer higher stability to the T1.6 loop. A structure-based first-principle energetic analysis (FIG. 7 and Table 6) predicts a favorable change in folding free energy of −1.7 kcal/mol for the stabilizing R236F mutation, underscoring the gain afforded by hydrophobic desolvation (−2.8 kcal/mol) as driving the increase in stability. This more than offsets the major destabilizing contribution, i.e., the loss of hydrogen bonding energy upon mutation (1.4 kcal/mol), between the carbonyl group of D207 and the guanidinium group of R236.

TABLE 6

| | Internal energy | | | | Desolvation | | Entropy | | | |
|---|---|---|---|---|---|---|---|---|---|---|
| Mutant | vdW | elec | hb | wb | hyd | pol | sc | mc | Calc[a] | Expt[b] |
| R236F | −0.24 | 0.22 | **1.40** | −0.07 | −1.24 | −1.54 | −0.23 | 0.01 | −1.68 | −1.38 |
| A31G/R236F | −0.09 | 0.22 | **1.40** | −0.07 | −0.97 | −1.81 | −0.31 | 0.17 | −1.45 | −1.08 |
| F70I | 0.70 | 0.01 | 0.00 | −0.02 | **1.42** | −0.75 | −0.18 | 0.18 | **1.37** | 0.59 |
| V187I | −0.35 | 0.00 | 0.00 | 0.00 | −0.83 | 0.13 | 0.25 | 0.09 | −0.70 | >0.73 |
| Y66V | **1.63** | 0.00 | **1.30** | 0.26 | **2.89** | −2.72 | −0.50 | −0.33 | **2.55** | NA |

[a]Total predicted folding free energy change upon mutation, $\Delta\Delta G_{fold}$ (kcal/mol), calculated as the sum of energetic contributions (kcal/mol), i.e., vdW + elec + hb + wb + hyd + pol + sc + mc, where vdW: van der Waals energy, elec: electrostatic energy, hb: hydrogen bond energy, wb: water bridge energy, hyd: hydrophobic desolvation free energy, pol: polar desolvation free energy, sc: side-chain entropic contribution, mc: main-chain entropic contribution. Calculations were done with the FOLD-X program (Guerios et al. 2002). Absolute contributions larger than 0.81 kcal/mol (the standard deviation of calibrated FOLD-X function) are in bold.

[b]Experimental stability data is expressed as fold-change in the half-time of inactivation upon mutation (Table 2), converted to logarithmic scale.

The double mutation A31G/R236F also does not introduce major variations relative to XcPL wild-type and R236F mutant structures. A noticeable change is a peptide flip at the A31G mutation site, bringing the backbone carbonyl of A30 closer to the side chain of K151 side chain that undergoes a concerted conformational change. The A31G mutation resides in the N-terminal region of the enzyme on the opposite side of the β-helix relative to the catalytic site. Thus the 2-fold increase in catalytic efficiency upon the A31G mutation cannot be accounted for by the present structural data. Mutations distant from catalytic sites are documented to be as effective as close mutations in improving enzymatic activity, but the underlying factors are often subtle and elude structural interpretations. Computational predictions yielded a marginal destabilizing effect (0.2 kcal/mol) for the A31G mutation in agreement with the experimental data (Table 2 and FIG. 7).

Figure 7:
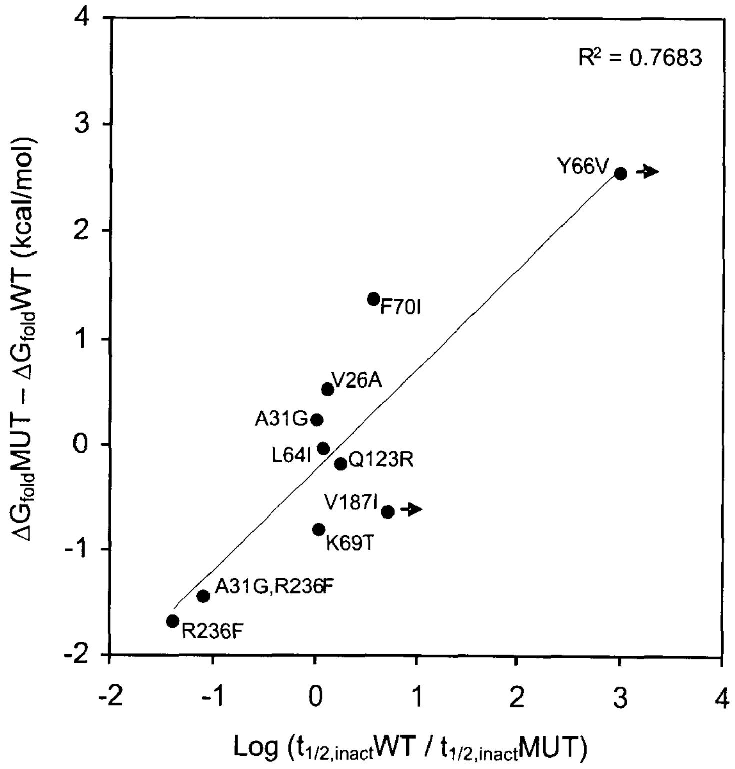
FIG. 7 depicts a graph of predicted folding free energies versus experimental stabilities of pectate lyase mutants relative to the wild-type protein. Predictions are based on the FOLD-X program using the crystal structure of the wild-type pectate lyase. Experimental stability data is expressed as fold-change in the half-time of inactivation upon mutation converted to logarithmic scale. Arrows indicate larger experimental changes than those plotted in the case of Y66V and V187I mutations.

The remaining single point mutations had either marginal or destabilizing effects on the thermal stability. A retrospective structural and computational analysis can rationalize why these single-amino acid substitutions did not materialize into improved thermostability of the target mesophilic enzyme (FIG. 7 and Table 6).

REFERENCES

The disclosures of the following references are incorporated herein by reference in their entirety.

Akin D. E., Foulk J. A., Dodd R. B. and McAlister D. D. 2001. Enzyme-retting of flax and characterization of processed fibers. *Journal of Biotechnology* 89: 193-203.

Andersen, L. N., et al. 2000. U.S. Pat. No. 6,124,127 issued Sep. 26, 2000.

Benen, J. A. E., Kester H., Parenicova L., and Visser J. 2000. Characterization of *Aspergillus niger* pectate lyase A. *Biochemistry* 39: 15563-15569.

Berensmeier S., Singh S. A., Meens J. and Buchholz K. 2004. Cloning of the pelA gene from *Bacillus licheniformis* 14A and biochemical characterization of recombinant, thermostable, high-alkaline pectate lyase. *Appl. Microbiol. Biotechnol.* 64: 560-567.

Bjornvad, M. E., et al. 2006. International Patent Publication WO 2001/079440 published Oct. 25, 2001.

Bradford M. 1976. A Rapid and Sensitive Method for the Quantitation of Microgram Quantities of Protein Utilizing the Principle of Protein-Dye Binding. *Anal. Biochem.* 72: 248-254.

Collmer A., J. L. Ried, and M. S. Mount. 1988. Assay methods for pectic enzymes. *Methods in Enzymology* 161: 329-335.

da Silva A. C. R., Ferro, J. A., Reinach, F. C., Farah, C. S., et al., 2002. Comparison of the genomes of two *Xanthomonas* pathogens with differing host specificities. *Nature* 417: 459-463.

Glad, S. S., et al. 2006. International Patent Publication WO 2006/0089283 published Apr. 26, 2006.

Guerios, R., J. E. Nielson, and L. Serrano. 2002. Predicting changes in the stability of proteins and protein complexes: a study of more than 1000 mutations. *J. Mol. Biol.* 320: 369-387.

Huertas-Gonzalez M. D, Ruiz-Roldán M., García-Maceira F., Roncero M., Di-Pietro A. 1999. Cloning and characterization of pl1 encoding an in planta-secreted pectate lyase of *Fusarium oxysporum. Current Genetics* 35: 36-40.

Klug-Santner B. G, et al. 2006. Purification and characterization of a new bioscouring pectate lyase from *Bacillus pumilus* BK2. *Journal of Biotechnology* 121: 390-401.

Kluskens L D, Gert-Jan W. M. Van Alebeek, Alphons G. J. Voragen, Willem M. D E Vos and John Van Der Oost. 2003. Molecular and biochemical characterization of the thermoactive family 1 pectate lyase from the hyperthermophilic bacterium *Thermotoga maritime. Biochem. J.* 370: 651-659.

Miller G. L. 1959. Use of dinitrosalicylic acid reagent for determination of reducing sugar. *Anal. Chem.* 31: 426-428.

Ossola M. and Galante Y. M. 2004. Scouring of flax rove with the aid of enzymes. *Enzyme and Microbial Technology* 34: 177-186.

Ouajai S., Shanks R. A. 2005. Morphology and Structure of Hemp Fiber after Bioscouring. *Macromolecular Bioscience* 5: 124-134.

Sambrook, J., E. F. Fritsch, and T. Maniatis. 1989. *Molecular Cloning: A Laboratory Manual,* 2nd edn. Cold Spring Harbor Laboratory Press, Cold Spring Harbor, N.Y.

Sawada K. and Ueda M. 2001. Enzyme processing of textiles in reverse micellar solution. *Journal of Biotechnology* 89: 263-269.

Showell, M. S., et al. 2000. International Patent Publication WO 2000/042152 published Jul. 20, 2000.

Smith, S. P., Barber, K. R., Dunn, S. D., Shaw, G. S. 1996. Structural influence of cation binding to recombinant human brain S100b: Evidence for calcium-induced exposure of a hydrophobic surface. *Biochem* 35: 8805-8814.

Solbak A. I., et al. 2005. Discovery of pectin-degrading enzymes and directed evolution of a novel pectate lyase for processing cotton fabric. *J. Biol. Chem.* 280: 9431-9438.

Takao, M., Nakaniwa, T., Yoshikawa, K., Terashita, T. and Sakai, T. 2001. Molecular cloning, DNA sequence, and expression of the gene encoding for thermostable pectate lyase of thermophilic *Bacillus* sp. TS 47. *Biosci. Biotechnol. Biochem.* 65: 322-329.

Tzanov T., Calafell M., Guebitz G. M. and Cavaco-Paulo A. 2001. Bio-preparation of cotton fabrics. *Enzyme and Microbial Technology* 29: 357-362.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

---

The invention claimed is:

1. Polypeptide comprising the amino acid sequence as set forth in SEQ ID NO: 2, wherein Xaa at position 31 is alanine or glycine and Xaa at position 236 is arginine or phenylalanine with the proviso that Xaa at position 236 is not arginine when Xaa at position 31 is alanine.

2. The polypeptide according to claim 1, wherein the amino acid sequence comprises SEQ ID NO: 3.

3. The polypeptide according to claim 1, wherein the amino acid sequence comprises SEQ ID NO: 4.

4. The polypeptide according to claim 1, wherein the amino acid sequence comprises SEQ ID NO: 5.

5. The polypeptide according to claim 1 that is isolated.

6. A process of isolating fibers from non-cellulosic material in a fiber plant comprising contacting raw fibers of the fiber plant with the polypeptide as claimed in claim 1 to enzymatically degrade the non-cellulosic material and separating the fibers from the degraded non-cellulosic material.

7. The process according to claim 6, wherein the non-cellulosic material comprises pectin.

8. The process according to claim 6, wherein the fiber plant is hemp, jute, flax, ramie or cotton.

9. The process of claim 6, wherein the contacting is done in aqueous medium at a pH in a range of from 4 to 10.

10. The process of claim 9, wherein the pH is in a range of from 8 to 9.

11. The process of claim 6, wherein the contacting is done at a temperature in a range of from 30° C. to 55° C.

12. The process of claim 11, wherein the temperature is in a range of from 40° C. to 50° C.

13. A process of degrading non-cellulosic material comprising contacting the non-cellulosic material with the polypeptide as claimed in claim 1, wherein the polypeptide enzymatically degrades the non-cellulosic material.

14. The process of claim 13, wherein the non-cellulosic material is a component in detergents, in textile processing, in cellulose fiber processing, in treatment of pectic wastewaters, in paper making, in coffee and tea fermentations or in clarification of fruit juices.

* * * * *